US012110268B1

(12) United States Patent
Nordahl

(10) Patent No.: US 12,110,268 B1
(45) Date of Patent: *Oct. 8, 2024

(54) INFUSING RAW CANNABINOIDS INTO FOOD OIL

(71) Applicant: Jeff Nordahl, Soquel, CA (US)

(72) Inventor: Jeff Nordahl, Soquel, CA (US)

( * ) Notice: Subject to any disclaimer, the term of this patent is extended or adjusted under 35 U.S.C. 154(b) by 637 days.

This patent is subject to a terminal disclaimer.

(21) Appl. No.: 17/206,397

(22) Filed: Mar. 19, 2021

Related U.S. Application Data

(63) Continuation of application No. 16/776,479, filed on Jan. 29, 2020, now Pat. No. 10,981,856, which is a continuation of application No. 16/108,090, filed on Aug. 21, 2018, now Pat. No. 10,597,348.

(60) Provisional application No. 62/548,308, filed on Aug. 21, 2017.

(51) Int. Cl.
*C07C 63/04* (2006.01)
*C07B 63/00* (2006.01)
*C07D 311/80* (2006.01)

(52) U.S. Cl.
CPC .............. *C07C 63/04* (2013.01); *C07B 63/00* (2013.01); *C07D 311/80* (2013.01)

(58) Field of Classification Search
CPC ........ C07C 63/04; C07B 63/00; C07D 311/80
See application file for complete search history.

(56) References Cited

U.S. PATENT DOCUMENTS

| 10,981,856 | B1* | 4/2021 | Nordahl | .................. C07B 63/00 |
| 2016/0106705 | A1 | 4/2016 | Verzura | ........................ 514/454 |
| 2017/0020942 | A1 | 1/2017 | Naheed | |
| 2018/0360103 | A1 | 12/2018 | Kaplan | |

* cited by examiner

*Primary Examiner* — Deborah D Carr
(74) *Attorney, Agent, or Firm* — Adibi IP Group, PC; Amir V. Adibi; Andrew C. Palmer

(57) ABSTRACT

A *cannabis* infused oil is formed by collecting and drying raw *cannabis* material having a desired cannabinoid profile. Next, the raw dried *cannabis* material is blended with oil to obtain a *cannabis* infused oil mixture. Blending is performed without causing the *cannabis* material to become decarboxylated. Next, the *cannabis* material is filtered from the *cannabis* infused oil mixture thereby obtaining a *cannabis* infused oil. The *cannabis* infused oil has at least two cannabinoids present in the oil in accordance with the desired cannabinoid profile. Next, the *cannabis* infused oil is packaged for storage and shipment. The *cannabis* infused oil is formed without any alcohol, does not have any decarboxylated cannabinoids and is non-psychoactive. In one example, the *cannabis* infused oil has between 100 milligrams and 2,000 milligrams of cannabinoids per fluid ounce of *cannabis* infused oil. In another example, before blending with oil, the *cannabis* material is combined with alcohol.

20 Claims, 18 Drawing Sheets

METHOD OF INFUSING RAW CANNABIS MATERIAL INTO CONSUMABLE OIL

METHOD OF INFUSING RAW CANNABIS MATERIAL INTO CONSUMABLE OIL

OBTAIN AND DRY RAW CANNABIS MATERIAL HAVING A DESIRED CANNABINOID PROFILE

| EXAMPLE CANNABINOID PROFILES |
|---|
| 40 CBDa : 1 THCa |
| 35 CBDa : 1 THCa |
| 30 CBDa : 1 THCa |
| 25 CBDa : 1 THCa |
| 20 CBDa : 1 THCa |
| 10 CBDa : 1 THCa |
| 5 CBDa : 1 THCa |
| 4 CBDa : 1 THCa |
| 3 CBDa : 1 THCa |
| 3 CBDa : 2 THCa |
| 2 CBDa : 1 THCa |
| 1 CBDa : 1 THCa |
| 1 CBDa : 2 THCa |
| 1 CBDa : 3 THCa |
| 2 CBDa : 3 THCa |
| 0 CBDa : 1 THCa |
| 1 CBDa : 0 THCa |

EXAMPLE CANNABINOID PROFILES OF OBTAINED RAW CANNABIS MATERIAL

FIG. 3

GRIND RAW CANNABIS MATERIAL

COMBINE GROUND CANNABIS MATERIAL
WITH ALCOHOL

BLEND ALCOHOL AND GROUND CANNABIS MIXTURE WITH OIL

FILTER CANNABIS MATERIAL FROM CANNABIS INFUSED OIL MIXTURE

PACKAGED CANNABIS INFUSED OIL

| CANNABINOID PROFILES OF CANNABIS INFUSED OIL |
|---|
| AMOUNT OF CBDa IN CANNABIS INFUSED OIL IS AT LEAST 5% (1/20) OF TOTAL CANNABINOIDS IN CANNABIS INFUSED OIL |
| AMOUNT OF CBDa IN CANNABIS INFUSED OIL IS AT LEAST 10% (1/10) OF TOTAL CANNABINOIDS IN CANNABIS INFUSED OIL |
| AMOUNT OF CBDa IN CANNABIS INFUSED OIL IS AT LEAST 20% (1/5) OF TOTAL CANNABINOIDS IN CANNABIS INFUSED OIL |
| AMOUNT OF CBDa IN CANNABIS INFUSED OIL IS AT LEAST 25% (1/4) OF TOTAL CANNABINOIDS IN CANNABIS INFUSED OIL |
| AMOUNT OF CBDa IN CANNABIS INFUSED OIL IS AT LEAST 30% (3/10) OF TOTAL CANNABINOIDS IN CANNABIS INFUSED OIL |
| AMOUNT OF CBDa IN CANNABIS INFUSED OIL IS AT LEAST 33.33% (1/3) OF TOTAL CANNABINOIDS IN CANNABIS INFUSED OIL |
| AMOUNT OF CBDa IN CANNABIS INFUSED OIL IS AT LEAST 40% (2/5) OF TOTAL CANNABINOIDS IN CANNABIS INFUSED OIL |
| AMOUNT OF CBDa IN CANNABIS INFUSED OIL IS AT LEAST 50% (1/2) OF TOTAL CANNABINOIDS IN CANNABIS INFUSED OIL |
| AMOUNT OF CBDa IN CANNABIS INFUSED OIL IS AT LEAST 60% (3/5) OF TOTAL CANNABINOIDS IN CANNABIS INFUSED OIL |
| AMOUNT OF CBDa IN CANNABIS INFUSED OIL IS AT LEAST 66.66% (2/3) OF TOTAL CANNABINOIDS IN CANNABIS INFUSED OIL |
| AMOUNT OF CBDa IN CANNABIS INFUSED OIL IS AT LEAST 70% (7/10) OF TOTAL CANNABINOIDS IN CANNABIS INFUSED OIL |
| AMOUNT OF CBDa IN CANNABIS INFUSED OIL IS AT LEAST 75% (3/4) OF TOTAL CANNABINOIDS IN CANNABIS INFUSED OIL |
| AMOUNT OF CBDa IN CANNABIS INFUSED OIL IS AT LEAST 80% (4/5) OF TOTAL CANNABINOIDS IN CANNABIS INFUSED OIL |
| AMOUNT OF CBDa IN CANNABIS INFUSED OIL IS AT LEAST 90% (9/10) OF TOTAL CANNABINOIDS IN CANNABIS INFUSED OIL |
| AMOUNT OF CBDa IN CANNABIS INFUSED OIL IS AT LEAST 95% OF TOTAL CANNABINOIDS IN CANNABIS INFUSED OIL |
| AMOUNT OF CBDa IN CANNABIS INFUSED OIL IS AT LEAST 99% OF TOTAL CANNABINOIDS IN CANNABIS INFUSED OIL |

CANNABINOID PROFILES OF CANNABIS INFUSED OIL FORMED IN FIG. 1

FIG. 11

| CANNABINOID PROFILES OF CANNABIS INFUSED OIL |
|---|
| AMOUNT OF THCa IN CANNABIS INFUSED OIL IS AT LEAST 5% (1/20) OF TOTAL CANNABINOIDS IN CANNABIS INFUSED OIL |
| AMOUNT OF THCa IN CANNABIS INFUSED OIL IS AT LEAST 10% (1/10) OF TOTAL CANNABINOIDS IN CANNABIS INFUSED OIL |
| AMOUNT OF THCa IN CANNABIS INFUSED OIL IS AT LEAST 20% (1/5) OF TOTAL CANNABINOIDS IN CANNABIS INFUSED OIL |
| AMOUNT OF THCa IN CANNABIS INFUSED OIL IS AT LEAST 25% (1/4) OF TOTAL CANNABINOIDS IN CANNABIS INFUSED OIL |
| AMOUNT OF THCa IN CANNABIS INFUSED OIL IS AT LEAST 30% (3/10) OF TOTAL CANNABINOIDS IN CANNABIS INFUSED OIL |
| AMOUNT OF THCa IN CANNABIS INFUSED OIL IS AT LEAST 33.33% (1/3) OF TOTAL CANNABINOIDS IN CANNABIS INFUSED OIL |
| AMOUNT OF THCa IN CANNABIS INFUSED OIL IS AT LEAST 40% (2/5) OF TOTAL CANNABINOIDS IN CANNABIS INFUSED OIL |
| AMOUNT OF THCa IN CANNABIS INFUSED OIL IS AT LEAST 50% (1/2) OF TOTAL CANNABINOIDS IN CANNABIS INFUSED OIL |
| AMOUNT OF THCa IN CANNABIS INFUSED OIL IS AT LEAST 60% (3/5) OF TOTAL CANNABINOIDS IN CANNABIS INFUSED OIL |
| AMOUNT OF THCa IN CANNABIS INFUSED OIL IS AT LEAST 66.66% (2/3) OF TOTAL CANNABINOIDS IN CANNABIS INFUSED OIL |
| AMOUNT OF THCa IN CANNABIS INFUSED OIL IS AT LEAST 70% (7/10) OF TOTAL CANNABINOIDS IN CANNABIS INFUSED OIL |
| AMOUNT OF THCa IN CANNABIS INFUSED OIL IS AT LEAST 75% (3/4) OF TOTAL CANNABINOIDS IN CANNABIS INFUSED OIL |
| AMOUNT OF THCa IN CANNABIS INFUSED OIL IS AT LEAST 80% (4/5) OF TOTAL CANNABINOIDS IN CANNABIS INFUSED OIL |
| AMOUNT OF THCa IN CANNABIS INFUSED OIL IS AT LEAST 90% (9/10) OF TOTAL CANNABINOIDS IN CANNABIS INFUSED OIL |
| AMOUNT OF THCa IN CANNABIS INFUSED OIL IS AT LEAST 95% OF TOTAL CANNABINOIDS IN CANNABIS INFUSED OIL |
| AMOUNT OF THCa IN CANNABIS INFUSED OIL IS AT LEAST 99% OF TOTAL CANNABINOIDS IN CANNABIS INFUSED OIL |

CANNABINOID PROFILES OF CANNABIS INFUSED OIL FORMED IN FIG. 1

FIG. 12

COLLECT AND DRY RAW CANNABIS MATERIAL
HAVING A DESIRED CANNABINOID PROFILE

BLEND RAW CANNABIS MATERIAL WITH OIL

PACKAGED CANNABIS INFUSED OIL
(NO ALCOHOL INVOLVED IN INFUSION PROCESS)

METHOD OF FORMING CANNABIS MATERIAL HAVING A DESIRED CANNABINOID PROFILE BY COMBINING TWO AMOUNT OF CANNABIS MATERIAL HAVING DIFFERENT CANNABINOID PROFILES (ANOTHER EMBODIMENT)

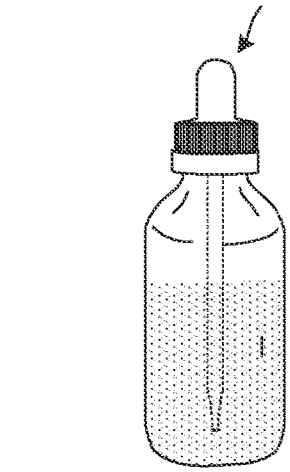
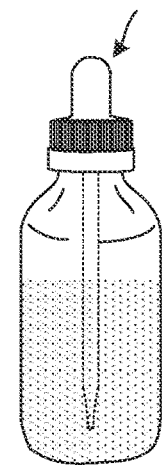
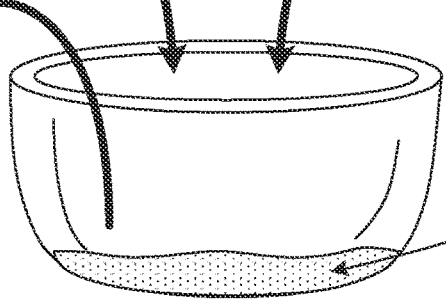
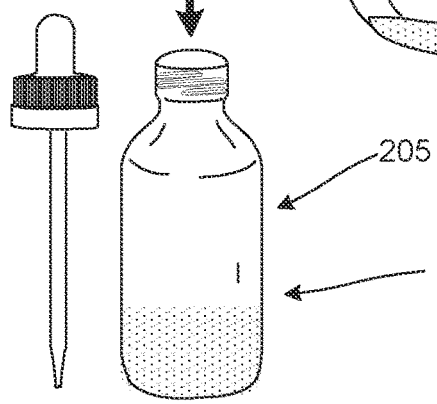
FORMING CANNABIS OIL HAVING A DESIRED CANNABINOID PROFILE FROM TWO CANNABIS OILS HAVING DIFFERENT CANNABINOID PROFILES
FIG. 19

INFUSING RAW CANNABINOIDS INTO FOOD OIL

CROSS-REFERENCE TO RELATED APPLICATIONS

This application is a continuation of, and claims the benefit under 35 U.S.C. § 120 from, nonprovisional U.S. patent application Ser. No. 16/776,479, entitled "Infusing Raw Cannabinoids Into Food Oil," filed on Jan. 29, 2020, now U.S. Pat. No. 10,981,856. U.S. patent application Ser. No. 16/776,479 is a continuation of, and claims the benefit under 35 U.S.C. § 120 from, nonprovisional U.S. patent application Ser. No. 16/108,090, entitled "Infusing Raw Cannabinoids Into Food Oil," filed on Aug. 21, 2018, now U.S. Pat. No. 10,597,348. U.S. patent application Ser. No. 16/108,090 in turn claims the benefit under 35 U.S.C. § 119 of U.S. provisional patent application Ser. No. 62/548,308, entitled "Infusing Raw Cannabinoids Into Food Oil," filed on Aug. 21, 2017. The subject matter of each of the foregoing documents is expressly incorporated herein by reference.

TECHNICAL FIELD

The present disclosure relates generally to methods for manufacturing and, and more particularly to manufacturing cannabinoid products.

BACKGROUND INFORMATION

The *cannabis* plant genus is known to produce over four hundred and eighty different chemical substances, and at least eighty of these chemical substances are classified as cannabinoids. Many cannabinoids have been found to have diverse medicinal uses which include analgesic, anti-inflammatory, anticancer, antibiotic, anti-anxiety, and antioxidant properties. There are now thousands of strains of the *cannabis* plant that have evolved naturally or have been developed through hybridization. The different strains of *cannabis* tend to contain different combinations of these cannabinoids in varying amounts.

Cannabinoids found in their natural state typically are in a non-decarboxylated form. Cannabinoids can be converted into a decarboxylated form by a process referred to as decarboxylation. Decarboxylation is a chemical reaction that removes the carboxyl group from a compound. In the case of cannabinoids, decarboxylation involves removing the carboxyl group from the cannabinoid compounds. One common technique for performing decarboxylation is by heating *cannabis* material to 240° F. or higher for ten minutes to a few hours. Decarboxylation also occurs in *cannabis* material if the material is allowed to be dry cured. These cannabinoids provide different medicinal benefits when they are in their 'raw' or non-decarboxylated form, compared to their properties after they are decarboxylated.

Two cannabinoids that show tremendous medicinal potential are tetrahydrocannabinol (THC) and cannabidiol (CBD). THC is the decarboxylated cannabinoid that is considered to be psychoactive. However, if the *cannabis* material is never heated, 'decarboxylated', the cannabinoid will remain in its acid form, tetrahydrocannabinolic acid (THCa). THCa is not considered to be psychoactive. THCa also provides many medicinal benefits without causing psychoactive effects for the user. Most notably, THCa has many anti-inflammatory and cancer cell fighting properties while not being psychoactive. The cannabinoid CBD also is present in the acid form, cannabidiolic acid (CBDa), if the raw *cannabis* material is not decarboxylated. But when decarboxylated, the CBDa is converted to CBD. Both CBDa and CBD have a different set of medicinal properties.

Because decarboxylation occurs when the *cannabis* material is heated, it is challenging to find methods for consumers to have access to the 'raw' non-decarboxylated *cannabis* material. Most extraction or infusion techniques rely on heat to extract the cannabinoids, or use heat to purge solvents used in the extraction process. As a result, commercial distribution of raw non-decarboxylated *cannabis* material has been commercially unfeasible.

Another technique is to infuse *cannabis* into olive oil or other food grade oil. Food grade *cannabis* infusions can be made from healthy food oils (olive oil, avocado oil, coconut oil, etc.), that taste great have a long shelf life, and they are easy to dose and consume. Many patients prefer *cannabis* infusions that are processed using only food ingredients (no petroleum solvents). Currently, many *cannabis* formulas delivered in a high concentrate oils that are a thick tar consistency that is nearly impossible to dose correctly, and these concentrates have a very unpleasant taste. Food oil infusions are the preferred medium for consumers, but achieving an efficient food oil infusion without the use of heat, which preserves the *cannabis* in its raw form, is currently not known. It is extremely difficult to efficiently extract cannabinoids in their raw form. It is even more difficult to efficiently extract the raw cannabinoids into olive oil without the use of heat or chemical solvents. Other raw extraction techniques, such as $CO_2$ super critical extraction, create a final product that is a thick tar that is difficult to handle, dose, and has an unpleasant taste, and these techniques often destroy or remove terpenes and other desirable plant compounds.

One known technique is to place the *cannabis* material in food oil, then heat the oil *cannabis* mixture. The heat causes the cannabinoids to infuse into the hot food oil, however, the heat also undesirably decarboxylates the cannabinoids thereby converting the raw THCa into THC and CBDa into CBD. Another known technique is to soak the *cannabis* material in an alcohol solution for a few days or weeks and filter the plant material out of the alcohol. This results in a raw *cannabis* alcohol tincture. This method extracts all of the raw cannabinoids, but the alcohol solution is extremely high in alcohol and has an unpleasant taste to many people. Moreover, many consumers do not want to consume high alcohol tinctures. It is common to then heat the alcohol to evaporate off the alcohol, but this heating undesirably decarboxylates the cannabinoids. A solution that overcomes these challenges is desired.

SUMMARY

Methods of manufacturing, packaging, and storing a *cannabis* infused oil are provided. In a first step, raw *cannabis* material is collected by trimming leaves or flowers of a *cannabis* plant. The raw *cannabis* material is then dried to a moisture content of 15% or less at a temperature below 125° F. to avoid decarboxylation. The raw *cannabis* material has a desired cannabinoid profile. In a second step, the raw *cannabis* material is grinded to obtain a ground *cannabis* material having the desired cannabinoid profile. In a third step, the ground *cannabis* material having the desired cannabinoid profile is combined with an alcohol, such as food grade ethanol or organic alcohol, to obtain an alcohol and ground *cannabis* mixture. The ground *cannabis* material is moistened with the alcohol and is combined with the alcohol without bathing the ground *cannabis* material in alcohol. The alcohol and ground *cannabis* mixture are lightly blended and left to sit for between one minute and two hours such that the *cannabis* material is moistened with the alcohol. In a fourth step, the alcohol and ground *cannabis* mixture are blended with oil. The oil selected for the infusion is a food grade oil, such as olive oil, vegetable oil, coconut oil, organic oil, or any other food grade oil. Lecithin is optionally added during the blending process. The lecithin increases the bio-availability of the cannabinoids when the finished oil infusion is consumed. The mixture is blended without causing the *cannabis* material to undergo a decarboxylation process. In one example, the mixture has 32 ounces of oil, 4 ounces of *cannabis*, and 2 ounces of ethanol, and the mixture is blended together for between one and five minutes while maintaining the temperature of the mixture below 125° F. thereby preventing the decarboxylation. One teaspoon to one tablespoon of soy-based or sunflower-based lecithin is optionally added during the blending process. In a fifth step, the *cannabis* material is filtered from the *cannabis* infused oil mixture thereby obtaining a *cannabis* infused oil. In a sixth step, the *cannabis* infused oil is packaged to obtain a packaged *cannabis* infused oil. The packaged *cannabis* infused oil does not have any decarboxylated cannabinoids. In one example, the *cannabis* infused oil has between 100 milligrams and 2,000 milligrams of cannabinoids per fluid ounce of *cannabis* infused oil.

The raw *cannabis* material collected in the first step includes leaves, flowers, stems, trichomes, and/or other plant material from the *cannabis* plant. The trimmed *cannabis* material has a particular cannabinoid profile that has desired therapeutic qualities. The cannabinoid profile indicates types and proportions of cannabinoids present in the *cannabis* material. Different types of *cannabis* plants exhibit different cannabinoid profiles that are beneficial for certain types of medical conditions. The cannabinoid profile for a specific plant can be determined by a laboratory capable of performing a full spectrum cannabinoid profiling and analysis. Such laboratories often employ High Performance Liquid Chromatography (HPLC/UV) to conduct the analysis.

In one example, the *cannabis* plant is selected such that the cannabinoid profile has tetrahydrocannabinolic acid (THCa) and cannabidiolic acid (CBDa) such that the THCa to CBDa ratio is 3 CBDa to 2 THCa. This means that for every 3.0 milligrams of CBDa in a unit of *cannabis* material, there is approximately 2.0 milligrams of THCa. In another example, the ratio of CBDa to THCa is taken from the group consisting of: 40:1, 35:1, 30:1, 35:1, 20:1, 5:1, 5:2, 5:3, 5:4, 10:1, 4:1, 4:3, 3:1, 3:2, 2:1, 1:1, 1:2, 1:3, 2:3, 3:4, 1:4, 1:10, 4:5, 3:5, 2:5, 1:5, 1:20, 1:25, 1:30, 1:35, 1:40 0:1, and 1:0. In yet another example, the amount of CBDa in the *cannabis* infused oil is at least a pre-determined percentage of the total cannabinoids in the *cannabis* infused oil, and the pre-determined percentage of CBDa is taken from the group consisting of: 5%, 10%, 20%, 25%, 30%, 33.33%, 40%, 50%, 60%, 66.66%, 70%, 75%, 80%, 90%, 95%, and 99%. In yet another example, the amount of THCa in the *cannabis* infused oil is at least a pre-determined percentage of the total cannabinoids in the *cannabis* infused oil, and the pre-determined percentage of THCa is taken from the group consisting of: 5%, 10%, 20%, 25%, 30%, 33.33%, 40%, 50%, 60%, 66.66%, 70%, 75%, 80%, 90%, 95%, and 99%. Decarboxylated cannabinoids are formed by heating raw *cannabis* material thereby converting THCa to THC. THC may have psychoactive properties. Because the non-decarboxylated *cannabis* infused oil does not include such decarboxylated cannabinoids, the *cannabis* infused oil is generally non-psychoactive. Thus, a person can consume the *cannabis* infused oil and obtain therapeutic benefits while still retaining his/her faculties to perform his/her ordinary daily routine.

In another embodiment, a *cannabis* infused oil is formed without using any alcohol or ethanol during infusion. In a first step, raw *cannabis* material is collected and dried. Leaves and/or flowers of a *cannabis* plant are trimmed to obtain raw *cannabis* material. The raw *cannabis* material is then dried to a moisture content of 15% or less at a temperature below 125° F. to avoid decarboxylation. The raw *cannabis* material has a desired cannabinoid profile. In a second step, the raw and dried *cannabis* material is blended with oil. The oil selected for the infusion is a food grade oil, such as olive oil, vegetable oil, coconut oil, organic oil, or any other food grade oil. Lecithin is optionally added during the blending process. The lecithin increases the bio-availability of the cannabinoids when the finished oil infusion is consumed. The mixture is blended without causing the *cannabis* material to undergo a decarboxylation process. In one example, the mixture has 32 ounces of oil and 4 ounces of *cannabis*. The mixture is blended together for between one and five minutes while maintaining the temperature of the mixture below 125° F. thereby preventing the decarboxylation. One teaspoon to one tablespoon of soy-based or sunflower-based lecithin is optionally added during the blending process. The *cannabis* material is optionally grounded before being blended with the oil. In a third step, the *cannabis* material is filtered from the *cannabis* infused oil mixture thereby obtaining a *cannabis* infused oil. In a fourth step, the *cannabis* infused oil is packaged to obtain a packaged *cannabis* infused oil. The packaged *cannabis* infused oil does not have any decarboxylated cannabinoids.

The packaged *cannabis* infused oil is formed without using any alcohol or ethanol. In one example, the *cannabis* infused oil has between 100 milligrams and 2,000 milligrams of cannabinoids per fluid ounce of *cannabis* infused oil. The ratio of CBDa to THCa is taken from the group consisting of: 40:1, 35:1. 30:1, 25:1, 20:1, 5:1, 5:2, 5:3, 5:4, 10:1, 4:1, 4:3, 3:1, 3:2, 2:1, 1:1, 1:2, 1:3, 2:3, 3:4, 1:4, 1:10, 4:5, 3:5, 2:5, 1:5, 1:20, 1:25, 1:30, 1:35, 1:40, 0:1, and 1:0. In another example, the amount of CBDa in the *cannabis* infused oil is at least a pre-determined percentage of the total cannabinoids in the *cannabis* infused oil, and the pre-determined percentage of CBDa is taken from the group consisting of: 5%, 10%, 20%, 25%, 30%, 33.33%, 40%, 50%, 60%, 66.66%, 70%, 75%, 80%, 90%, 95%, and 99%. In yet another example, the amount of THCa in the *cannabis* infused oil is at least a pre-determined percentage of the total cannabinoids in the *cannabis* infused oil, and the pre-determined percentage of THCa is taken from the group consisting of: 5%, 10%, 20%, 25%, 30%, 33.33%, 40%, 50%, 60%, 66.66%, 70%, 75%, 80%, 90%, 95%, and 99%.

The foregoing is a summary and thus contains, by necessity, simplifications, generalizations and omissions of detail; consequently it is appreciated that the summary is illustrative only. Still other methods, and structures and details are set forth in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 3 is a diagram of a table showing cannabinoid profiles of different strains of *cannabis* plants.

FIG. 11 is a diagram of a table showing various CBDa-based cannabinoid profiles of *cannabis* infused oil that are obtainable using the technique of method 10.

FIG. 12 is a diagram of a table showing various THCa-based cannabinoid profiles of *cannabis* infused oil that are obtainable using the technique of method 10.

IG. 16 is a perspective diagram showing how *cannabis* material is separated from the oil to obtain a *cannabis* infused oil as in a third step of method 100.

Figure 17:
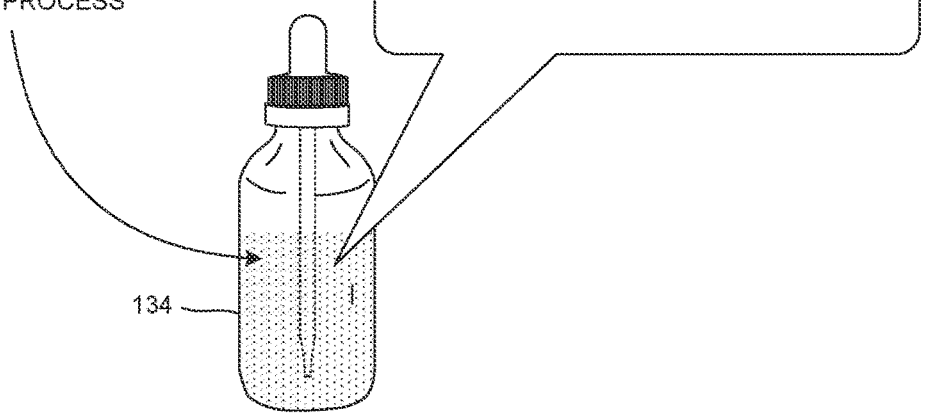

FIG. 17 is a perspective diagram of a packaged *cannabis* infused oil as in a fourth step of method 100.

Figure 18:
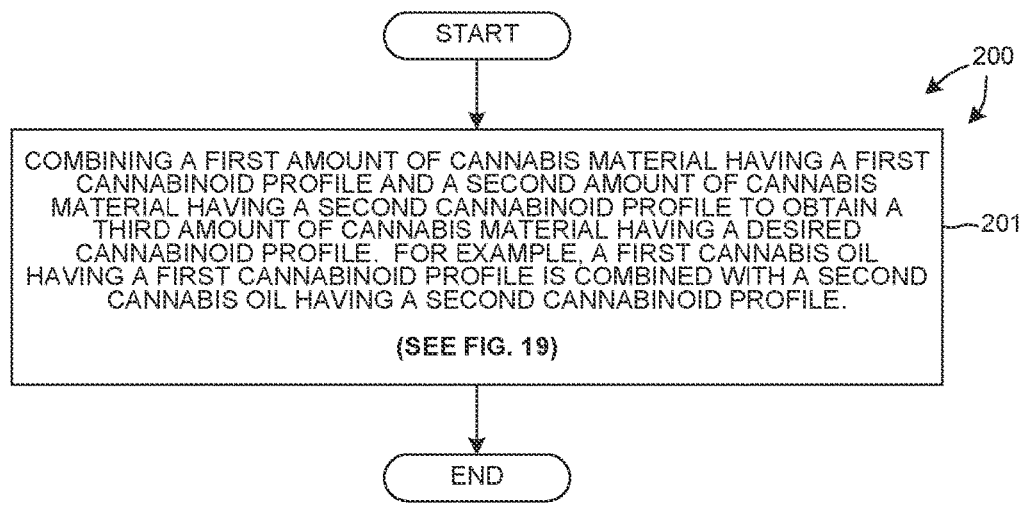

FIG. 18 is a flowchart of a method 200 in accordance with another embodiment.

FIG. 19 is a perspective diagram that shows how *cannabis* oil having a desired cannabinoid profile is formed by combining two *cannabis* oils having different cannabinoid profiles.

Reference will now be made in detail to some embodiments of the invention, examples of which are illustrated in the accompanying drawings.

DETAILED DESCRIPTION

Figure 1:
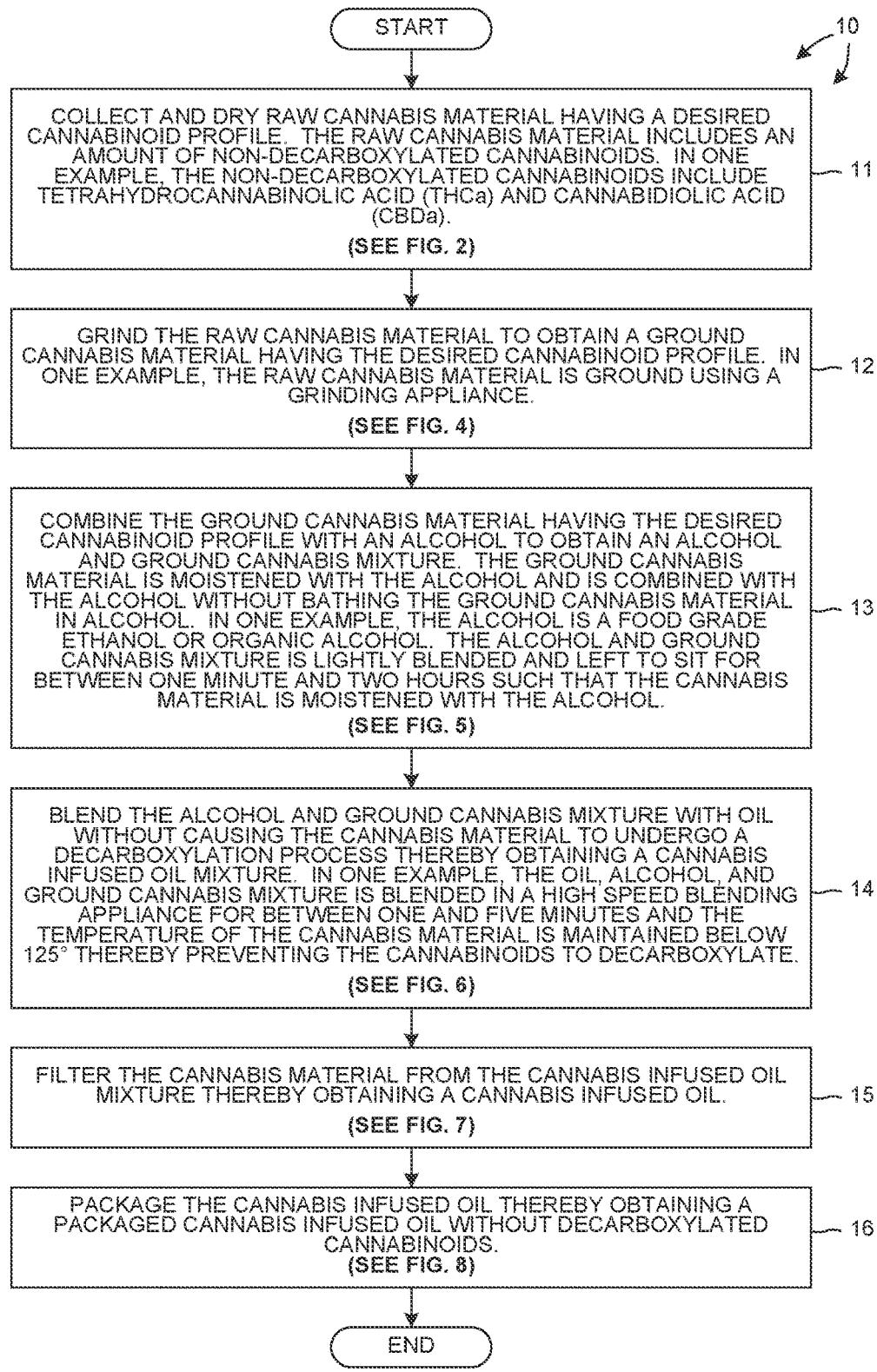
FIG. 1 is a flowchart of a method 10 in accordance with one embodiment.

FIG. 1 is a flowchart of a method 10 in accordance with one embodiment. The method 10 is a method of infusing raw *cannabis* material into a consumable oil.

In a first step (step 11), raw *cannabis* material having a desired cannabinoid profile is collected and dried. The raw *cannabis* material includes an amount of non-decarboxylated cannabinoids. The raw *cannabis* material includes leaves, flowers, stems, trichomes, and other plant material from the *cannabis* plant. The trimmed *cannabis* material has a particular cannabinoid profile that has desired therapeutic qualities. The cannabinoid profile indicates types and proportions of cannabinoids present in the *cannabis* material. Different types of *cannabis* plants exhibit different cannabinoid profiles that are beneficial for certain types of medical conditions. For example, in FIG. 2, raw *cannabis* material 20 is collected by trimming leaves 21 from the *cannabis* plant 22. The *cannabis* material 20 comprises non-decarboxylated cannabinoids that include tetrahydrocannabinolic acid (THCa) and cannabidiolic acid (CBDa).

After collection of the *cannabis* material, the *cannabis* material undergoes a drying process. In one embodiment, the raw *cannabis* material is dried to a moisture content of 35% or less. In another embodiment, the raw *cannabis* material is dried to a moisture content of 25% or less. In another embodiment, the raw *cannabis* material is dried to a moisture content of 15% or less. The raw *cannabis* material is dried by being kept in a storage area for one to five days. Air is circulated throughout the storage area using a fan or air ventilation system.

FIG. 3 is a diagram of a table 23 showing various cannabinoid profiles. The cannabinoid profile for a specific plant can be determined by a laboratory capable of performing a full spectrum cannabinoid profiling and analysis. Such laboratories often employ High Performance Liquid Chromatography (HPLC/UV) to conduct the analysis.

Figure 2:
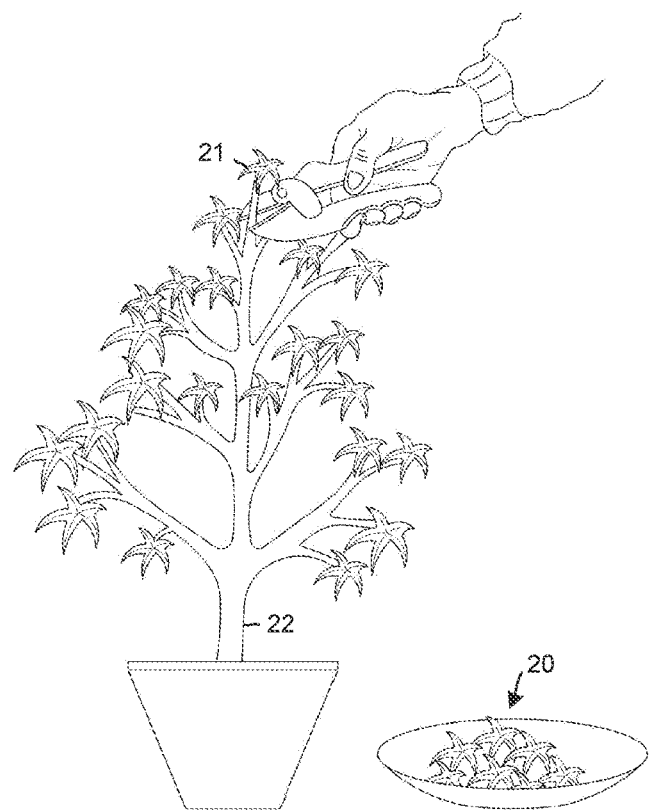
FIG. 2 is a perspective diagram showing how raw *cannabis* material 20 is collected and dried by trimming leaves from the *cannabis* plant as in a first step of method 10.

The *cannabis* plant 22 is cultivated to have a specific cannabinoid profile. Different cannabinoid profiles yield different therapeutic benefits appreciated by an artisan of ordinary skill in the *cannabis* arts. In this example, the *cannabis* plant 22 has a cannabinoid profile that includes tetrahydrocannabinolic acid (THCa) and cannabidiolic acid (CBDa). The *cannabis* plant 22 is selected having a cannabinoid profile where the amount of THCa and CBDa is present in a desired ratio. In the example of FIG. 2, the ratio is 3 CBDa to 2THCa. In other examples, the ratio of CBDa to THCa is taken from the group consisting of: 40:1, 35:1, 30:1, 25:1, 20:1, 5:1, 5:2, 5:3, 5:4, 10:1, 4:1, 4:3, 3:1, 3:2, 2:1, 1:1, 1:2, 1:3, 2:3, 3:4, 1:4, 1:10, 4:5, 3:5, 2:5, 1:5, 1:20, 1:25, 1:30, 1:35, 1:40, 0:1, and 1:0. Other ratios of CBDa to THCa are selectable depending on the therapeutic benefits that are desired.

In other embodiments, the cannabinoid profile includes cannabinoids in addition to CBDa and THCa. For example, other cannabinoids include cannabigerolic acid (CBGa), cannabigerovarin acid (CBGVa), tetrahydrocannabinolic acid (THCa), tetrahydrocannabivarin carboxylic acid (THCVa), cannabidiolic acid (CBDa), cannabidivarin acid (CBDVa), cannabichrome carboxylic acid (CBCa), cannabichrome varinic acid (CBCVa), tetrahydrocannabinol (THC), tetrahydrocannabivarin (THCV), tetrahydrocannabivarin acid (THVa), cannabidiol (CBD), cannabidivarin (CBDV), cannabichromene (CBC), cannabichromevarin (CBCV), cannabigerol (CBG), cannabigerovarin (CBGV), cannabinerolic acid (CBNa), cannabigerovarinic acid (CBNVa), cannabinol (CBN), cannabicyclol (CBL), and cannabicyclol acid (CBLa). The cannabinoid profile involves at least one of the above cannabinoids. In other examples, the cannabinoid profile of the selected *cannabis* plant has at least two of the above cannabinoids present in a desired ratio.

Figure 4:
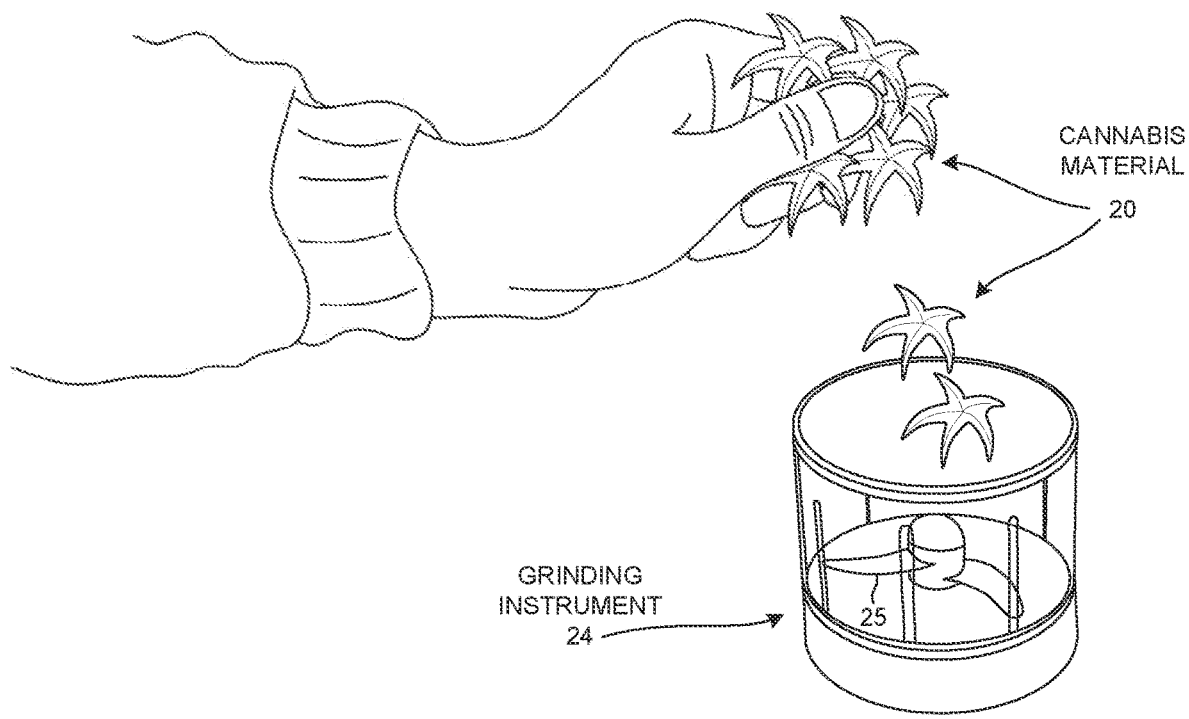
FIG. 4 is a perspective diagram showing how *cannabis* material is deposited into a grinding instrument as in a second step of method 10.

In a second step (step 12), the raw *cannabis* material is grinded to obtain a ground *cannabis* material having the desired cannabinoid profile. In one example, the raw *cannabis* material is ground using a grinding appliance. For example, in FIG. 4, the *cannabis* material 20 is deposited into a grinding instrument 24 having blades 25 that are actuated by an electric motor (not shown). When the grinding instrument 24 is activated, the blades 25 rotate and grind the *cannabis* material 20 into a powder consistency.

Figure 5:
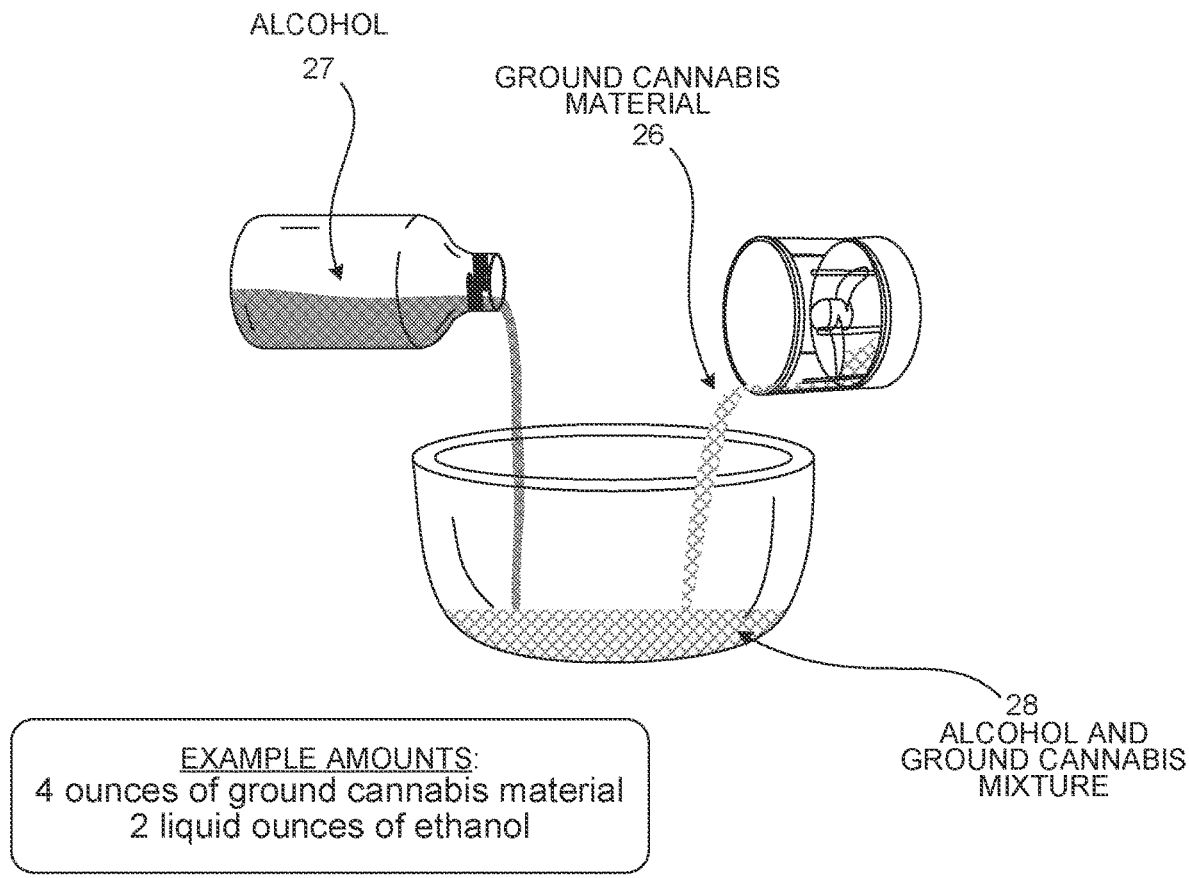
FIG. 5 is a perspective diagram showing how the *cannabis* material is moistened with alcohol as in a third step of method 10.

In a third step (step 13), the ground *cannabis* material having the desired cannabinoid profile is combined with an alcohol to obtain an alcohol and ground *cannabis* mixture. The ground *cannabis* material is moistened with the alcohol and is combined with the alcohol without bathing the ground *cannabis* material in alcohol. In one example, the alcohol is a food grade ethanol or organic alcohol. The alcohol and ground *cannabis* mixture is lightly blended and left to sit for between one minute and two hours such that the *cannabis* material is moistened with the alcohol. For example, in FIG. 5, ground *cannabis* material 26 is moistened with alcohol 27. In this example, 2 ounces of food grade ethanol is combined with 4 ounces of *cannabis* material. The ground *cannabis* material 26 is not saturated with the alcohol 27, rather the ground *cannabis* material 26 is lightly moistened. The alcohol and ground *cannabis* mixture 28 never has more alcohol 27 by weight than ground *cannabis* material 26. The mixture 28 is mixed or lightly blended so that the mixture is thoroughly mixed, and the alcohol is evenly distributed. The mixture 28 is left to sit for a period of time. In this example, the period of time is between one minute and two hours. During the time period, the ethanol 27 breaks down trichomes in the *cannabis* material 20 into the ethanol 27 such that the cannabinoids and other compounds are available for oil infusion.

Figure 6:
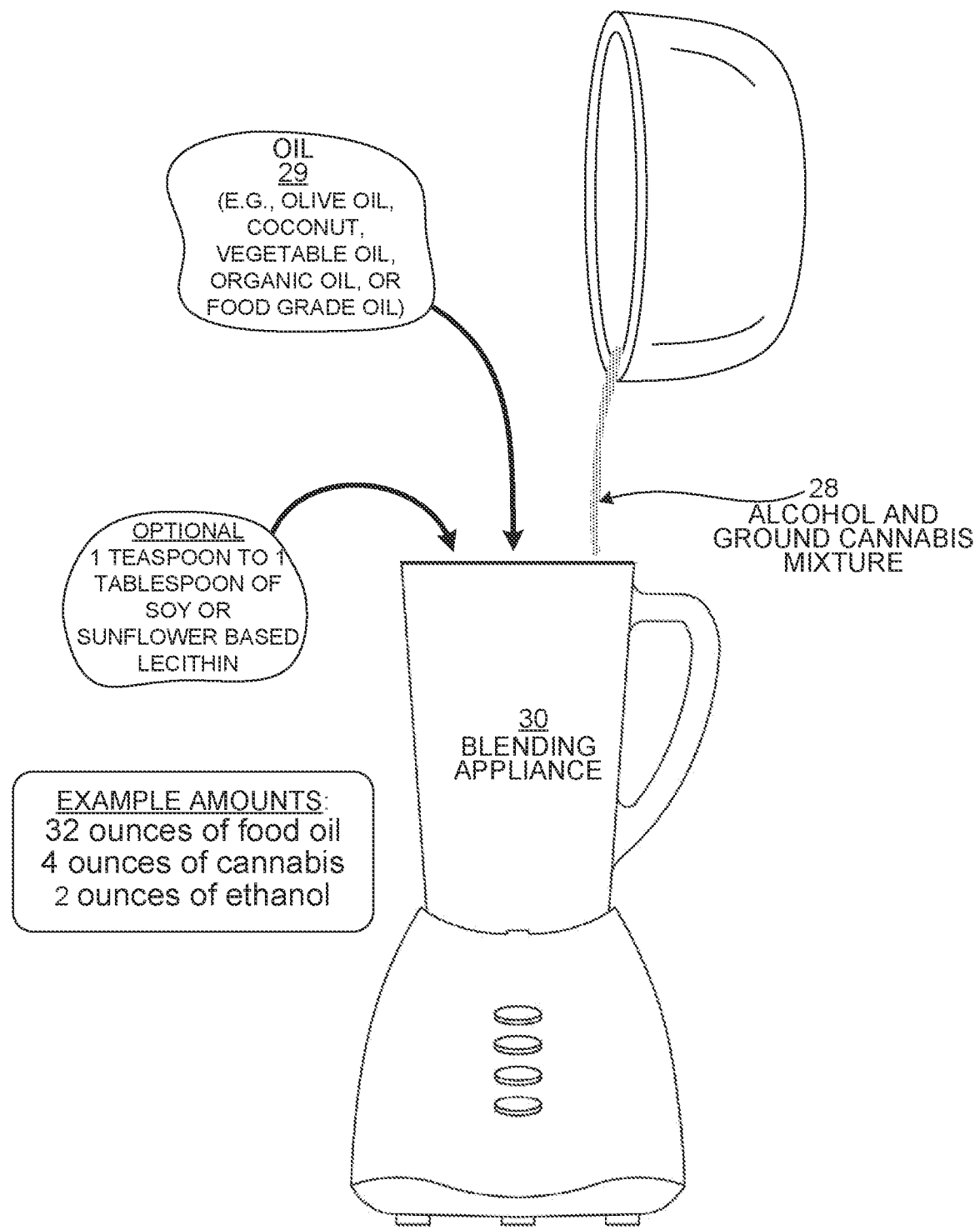
FIG. 6 is a perspective diagram showing how the alcohol and *cannabis* material mixture is blended with oil as in a fourth step of method 10.

In a fourth step (step 14), the alcohol and ground *cannabis* mixture are blended with oil. The mixture is blended without causing the *cannabis* material to undergo a decarboxylation process thereby obtaining a *cannabis* infused oil mixture. In the example of FIG. 6, the alcohol and ground *cannabis* mixture 28 is blended with 32 ounces of oil 29 in a high-speed blending appliance 30 for between one and five minutes. Oil 29 is selected from the group consisting of: olive oil, vegetable oil, coconut oil, organic oil, or any other food grade oil. During the blending process, the temperature of the *cannabis* material is maintained below 125° F. thereby preventing the cannabinoids from decarboxylating.

In addition to blending with oil, lecithin is optionally added during the blending process. The lecithin promotes the bio-availability of cannabinoids in the final oil infusion that is formed using novel method 10. One teaspoon to one tablespoon of soy-based or sunflower-based lecithin is optionally added during the blending process.

In a fifth step (step 15), the *cannabis* material is filtered from the *cannabis* infused oil mixture thereby obtaining a *cannabis* infused oil. For example, in FIG. 7, the *cannabis* infused oil mixture 31 is filtered using a food grade mesh and tincture system 32 to separate *cannabis* material to obtain a *cannabis* infused oil 33. In one embodiment, the food grade mesh and tincture system 32 comprises a fine weaved press bag and a cold press juicer. The *cannabis* infused oil mixture 31 is deposited into the fine weaved press bag and the fine weaved press bag is pressed between two plates of the cold press juicer. The *cannabis* infused oil 33 is filtered out of the fine weaved press bag and is stored in container 35. The extracted *cannabis* material remains in the fine weaved press bag. Once in the *cannabis* infused oil 33 is filtered into the container 35, the *cannabis* infused oil 33 is ready for packaging, such as packaging into tincture bottle 34.

Figure 8:
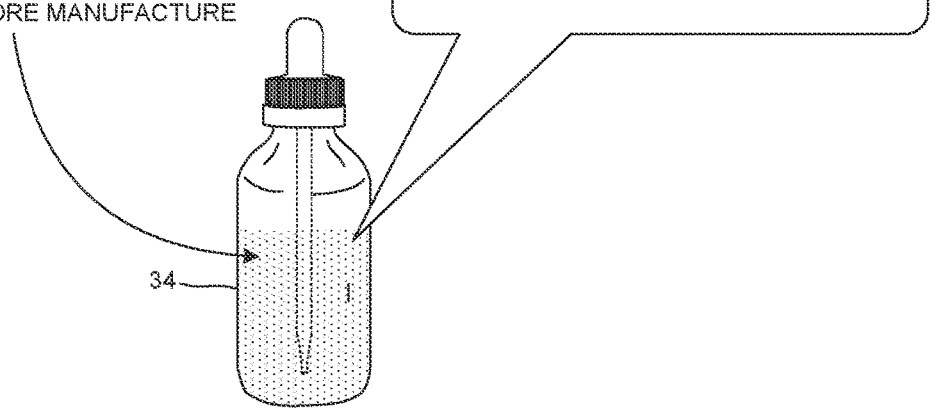
FIG. 8 is a perspective diagram of a packaged *cannabis* infused oil as in a sixth step of method 10.

In a sixth step (step 16), the *cannabis* infused oil is packaged thereby obtaining a packaged *cannabis* infused oil without decarboxylated cannabinoids. For example, in FIG. 8, the *cannabis* infused oil 33 is packaged in a container 34. The *cannabis* infused oil 33 has between 100 milligrams and 2,000 milligrams of cannabinoids per fluid ounce of *cannabis* infused oil 33. Any alcohol remaining in the *cannabis* infused oil 33 is typically less than 10% of the alcohol used in the process, but usually below 5% because much of the alcohol evaporates off during the blending process of the fourth step.

Figure 9:
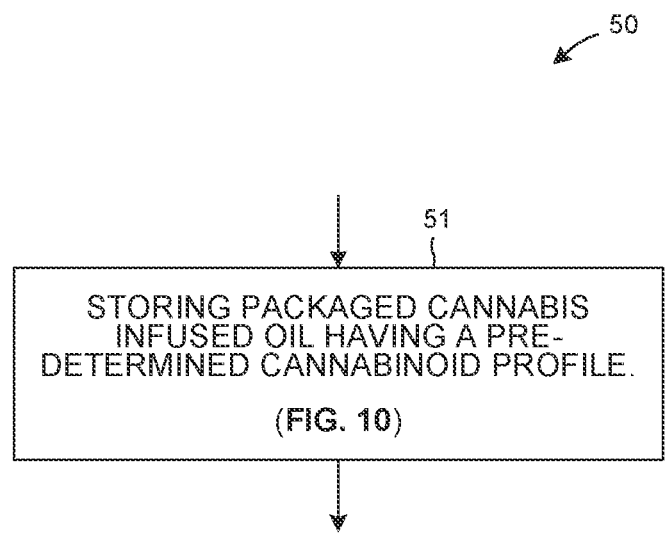
FIG. 9 is a flowchart of a method 50 in accordance with another embodiment.

FIG. 9 is a flowchart of a method 50 to store packaged containers having *cannabis* infused oil. In a first step (step 51), packaged *cannabis* infused oil containers having a *cannabis* infused oil are stored. For example, in FIG. 10, containers 52 each having a *cannabis* infused oil are stored on a shelf 53. The shelf 53 may be part of a retail-store, a dispensary, a storage facility, or a transport vehicle.

FIG. 11 is a diagram of a table 54 showing various CBDa-based cannabinoid profiles of *cannabis* infused oil that are obtainable using the technique of method 10. The cannabinoid profiles set forth in table 54 involve a pre-determined percentage of CBDa with respect to the total amount of cannabinoids in the *cannabis* infused oil. The remaining cannabinoids other than the pre-determined amount of CBDa comprises one of the cannabinoids set forth above or comprises a combination of the cannabinoids described above.

In one example, *cannabis* infused oil is obtained using the method 10 of FIG. 1 such that the amount of CBDa in the *cannabis* infused oil is at least 5% (or 1/20) of the total cannabinoids in the *cannabis* infused oil. In another example, *cannabis* infused oil is obtained using the method 10 of FIG. 1 such that the amount of CBDa in the *cannabis* infused oil is at least 10% (or 1/10) of the total cannabinoids in the *cannabis* infused oil. In another example, *cannabis* infused oil is obtained using the method 10 of FIG. 1 such that the amount of CBDa in the *cannabis* infused oil is at least 20% (or 1/5) of the total cannabinoids in the *cannabis* infused oil. In another example, *cannabis* infused oil is obtained using the method 10 of FIG. 1 such that the amount of CBDa in the *cannabis* infused oil is at least 25% (or 1/4) of the total cannabinoids in the *cannabis* infused oil. In another example, *cannabis* infused oil is obtained using the method 10 of FIG. 1 such that the amount of CBDa in the *cannabis* infused oil is at least 30% (or 3/10) of the total cannabinoids in the *cannabis* infused oil. In another example, *cannabis* infused oil is obtained using the method 10 of FIG. 1 such that the amount of CBDa in the *cannabis* infused oil is at least 33.33% (or 1/3) of the total cannabinoids in the *cannabis* infused oil. In another example, *cannabis* infused oil is obtained using the method 10 of FIG. 1 such that the amount of CBDa in the *cannabis* infused oil is at least 40% (or 2/5) of the total cannabinoids in the *cannabis* infused oil. In another example, *cannabis* infused oil is obtained using the method 10 of FIG. 1 such that the amount of CBDa in the *cannabis* infused oil is at least 50% (or 1/2) of the total cannabinoids in the *cannabis* infused oil. In another example, *cannabis* infused oil is obtained using the method 10 of FIG. 1 such that the amount of CBDa in the *cannabis* infused oil is at least 60% (or 3/5) of the total cannabinoids in the *cannabis* infused oil. In another example, *cannabis* infused oil is obtained using the method 10 of FIG. 1 such that the amount of CBDa in the *cannabis* infused oil is at least 66.66% (or 2/3) of the total cannabinoids in the *cannabis* infused oil. In another example, *cannabis* infused oil is obtained using the method 10 of FIG. 1 such that the amount of CBDa in the *cannabis* infused oil is at least 70% (or 7/10) of the total cannabinoids in the *cannabis* infused oil. In another example, *cannabis* infused oil is obtained using the method 10 of FIG. 1 such that the amount of CBDa in the *cannabis* infused oil is at least 75% (or 3/4)

of the total cannabinoids in the *cannabis* infused oil. In another example, *cannabis* infused oil is obtained using the method 10 of FIG. 1 such that the amount of CBDa in the *cannabis* infused oil is at least 80% (or ⅘) of the total cannabinoids in the *cannabis* infused oil. In another example, *cannabis* infused oil is obtained using the method 10 of FIG. 1 such that the amount of CBDa in the *cannabis* infused oil is at least 90% (or 9/10) of the total cannabinoids in the *cannabis* infused oil. In another example, *cannabis* infused oil is obtained using the method 10 of FIG. 1 such that the amount of CBDa in the *cannabis* infused oil is at least 99% of the total cannabinoids in the *cannabis* infused oil.

FIG. 12 is a diagram of a table 55 showing various THCa-based cannabinoid profiles of *cannabis* infused oil that are obtainable using the technique of method 10. The cannabinoid profiles set forth in table 55 involve a pre-determined percentage of THCa with respect to the total amount of cannabinoids in the *cannabis* infused oil. The remaining cannabinoids other than the pre-determined amount of THCa comprises one of the cannabinoids set forth above or comprises a combination of the cannabinoids described above.

In one example, *cannabis* infused oil is obtained using the method 10 of FIG. 1 such that the amount of THCa in the *cannabis* infused oil is at least 5% (or 1/20) of the total cannabinoids in the *cannabis* infused oil. In another example, *cannabis* infused oil is obtained using the method 10 of FIG. 1 such that the amount of THCa in the *cannabis* infused oil is at least 10% (or 1/10) of the total cannabinoids in the *cannabis* infused oil. In another example, *cannabis* infused oil is obtained using the method 10 of FIG. 1 such that the amount of THCa in the *cannabis* infused oil is at least 20% (or ⅕) of the total cannabinoids in the *cannabis* infused oil. In another example, *cannabis* infused oil is obtained using the method 10 of FIG. 1 such that the amount of THCa in the *cannabis* infused oil is at least 25% (or ¼) of the total cannabinoids in the *cannabis* infused oil. In another example, *cannabis* infused oil is obtained using the method 10 of FIG. 1 such that the amount of THCa in the *cannabis* infused oil is at least 30% (or 3/10) of the total cannabinoids in the *cannabis* infused oil. In another example, *cannabis* infused oil is obtained using the method 10 of FIG. 1 such that the amount of THCa in the *cannabis* infused oil is at least 33.33% (or ⅓) of the total cannabinoids in the *cannabis* infused oil. In another example, *cannabis* infused oil is obtained using the method 10 of FIG. 1 such that the amount of THCa in the *cannabis* infused oil is at least 40% (or ⅖) of the total cannabinoids in the *cannabis* infused oil. In another example, *cannabis* infused oil is obtained using the method 10 of FIG. 1 such that the amount of THCa in the *cannabis* infused oil is at least 50% (or ½) of the total cannabinoids in the *cannabis* infused oil. In another example, *cannabis* infused oil is obtained using the method 10 of FIG. 1 such that the amount of THCa in the *cannabis* infused oil is at least 60% (or ⅗) of the total cannabinoids in the *cannabis* infused oil. In another example, *cannabis* infused oil is obtained using the method 10 of FIG. 1 such that the amount of THCa in the *cannabis* infused oil is at least 66.66% (or ⅔) of the total cannabinoids in the *cannabis* infused oil. In another example, *cannabis* infused oil is obtained using the method 10 of FIG. 1 such that the amount of THCa in the *cannabis* infused oil is at least 70% (or 7/10) of the total cannabinoids in the *cannabis* infused oil. In another example, *cannabis* infused oil is obtained using the method 10 of FIG. 1 such that the amount of THCa in the *cannabis* infused oil is at least 75% (or ¾) of the total cannabinoids in the *cannabis* infused oil. In another example, *cannabis* infused oil is obtained using the method 10 of FIG. 1 such that the amount of THCa in the *cannabis* infused oil is at least 80% (or ⅘) of the total cannabinoids in the *cannabis* infused oil. In another example, *cannabis* infused oil is obtained using the method 10 of FIG. 1 such that the amount of THCa in the *cannabis* infused oil is at least 90% (or 9/10) of the total cannabinoids in the *cannabis* infused oil. In another example, *cannabis* infused oil is obtained using the method 10 of FIG. 1 such that the amount of THCa in the *cannabis* infused oil is at least 99% of the total cannabinoids in the *cannabis* infused oil.

Figure 13:
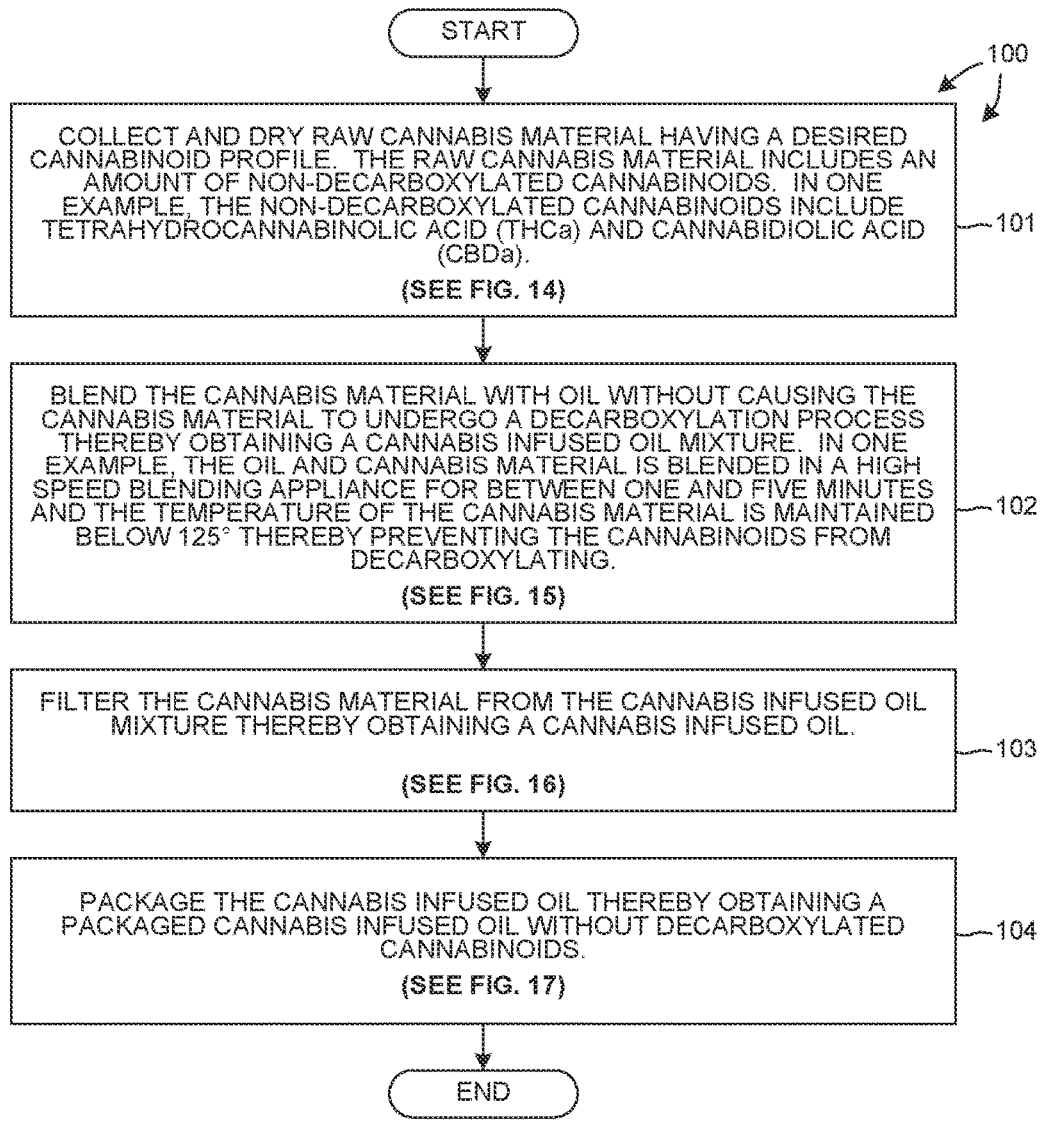
FIG. 13 is a flowchart of a method 100 in accordance with another embodiment.

FIG. 13 is a flowchart of a method 100 in accordance with another novel aspect. The method 100 is a method of infusing raw *cannabis* material into a consumable oil without using any alcohol or ethanol in the infusion process.

In a first step (step 101), raw *cannabis* material having a desired cannabinoid profile is collected and dried. The raw *cannabis* material includes an amount of non-decarboxylated cannabinoids. The raw *cannabis* material includes leaves, flowers, stems, trichomes, and other plant material from the *cannabis* plant. The trimmed *cannabis* material has a particular cannabinoid profile that has desired therapeutic qualities. The cannabinoid profile indicates types and proportions of cannabinoids present in the *cannabis* material. Different types of *cannabis* plants exhibit different cannabinoid profiles that are beneficial for certain types of medical conditions. For example, in FIG. 14, raw *cannabis* material 120 is collected by trimming leaves 121 from the *cannabis* plant 122. The *cannabis* material 120 comprises non-decarboxylated cannabinoids that include tetrahydrocannabinolic acid (THCa) and cannabidiolic acid (CBDa).

After collection of the *cannabis* material, the *cannabis* material undergoes a drying process. In one embodiment, the raw *cannabis* material is dried to a moisture content of 35% or less. In another embodiment, the raw *cannabis* material is dried to a moisture content of 25% or less. In another embodiment, the raw *cannabis* material is dried to a moisture content of 15% or less. The raw *cannabis* material is dried by being kept in a storage area for one to five days. Air is circulated throughout the storage area using a fan or air ventilation system.

Figure 14:
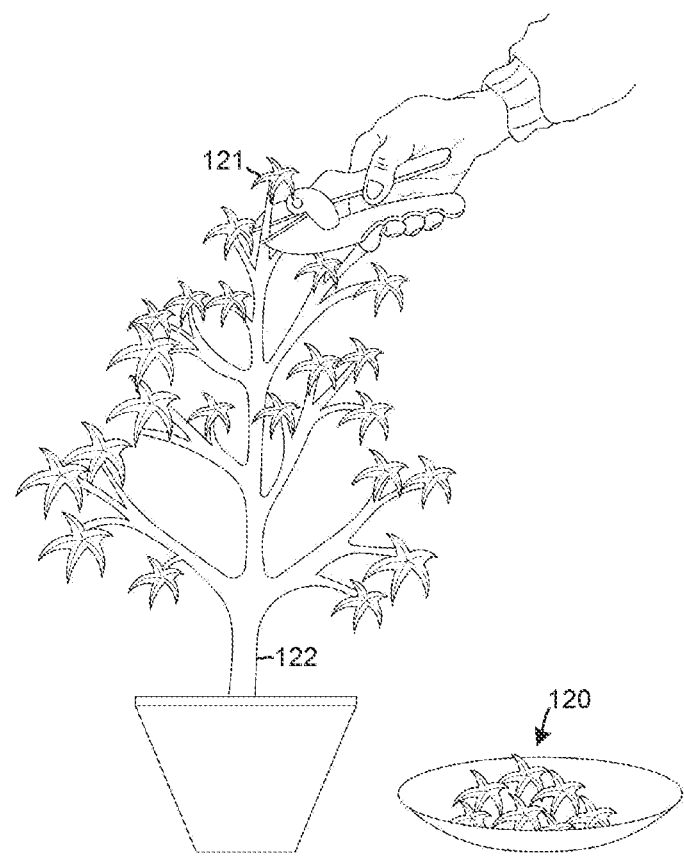
FIG. 14 is a perspective diagram showing how raw *cannabis* material 120 is collected and dried by trimming leaves from the *cannabis* plant as in a first step of method 100.
Figure 15:
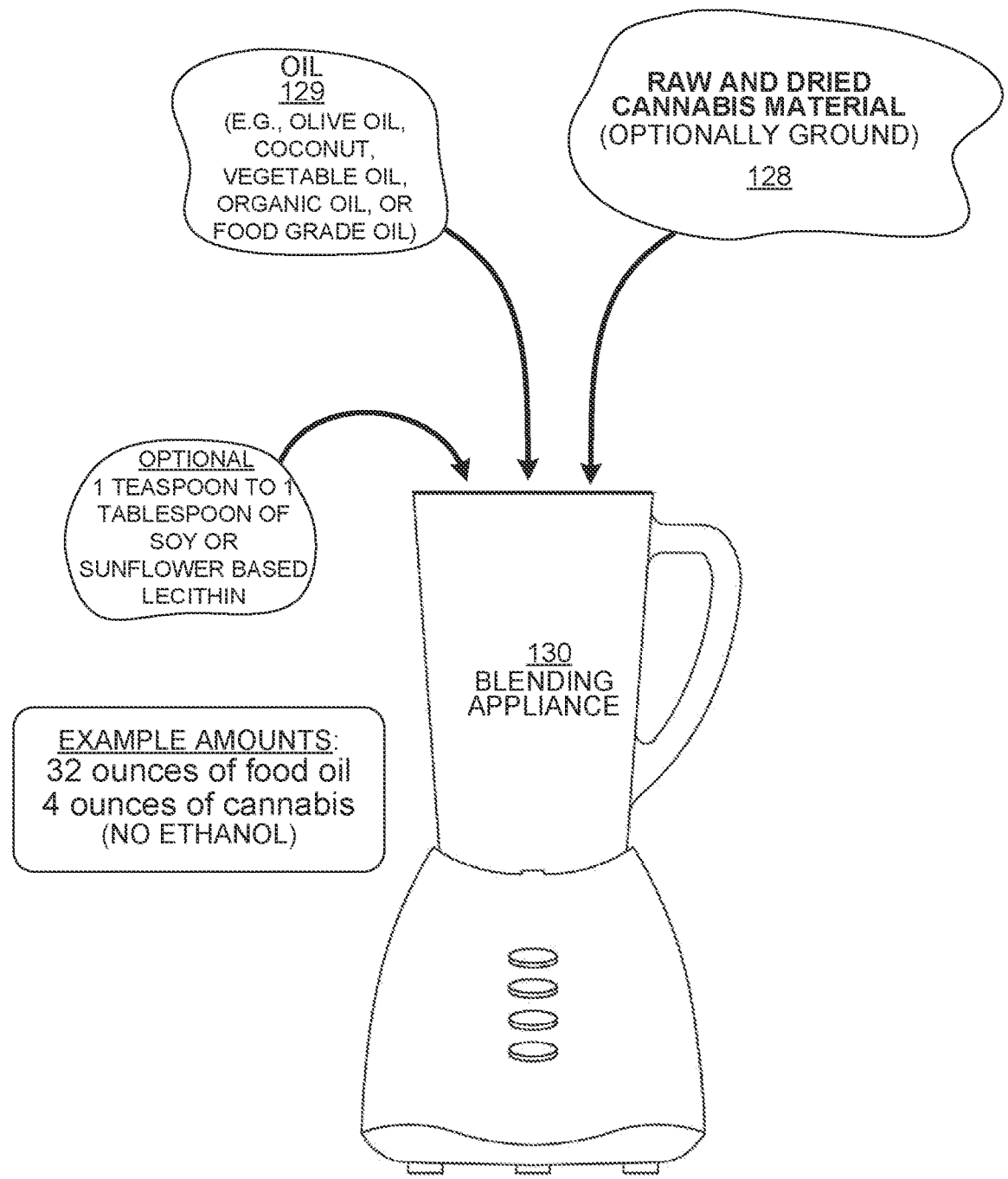
FIG. 15 is a perspective diagram showing how the ground *cannabis* material is blended with oil as in a second step of method 100.

The *cannabis* plant 122 is cultivated to have a specific cannabinoid profile. Different cannabinoid profiles yield different therapeutic benefits appreciated by an artisan of ordinary skill in the *cannabis* arts. In this example, the *cannabis* plant 122 has a cannabinoid profile that includes tetrahydrocannabinolic acid (THCa) and cannabidiolic acid (CBDa). The *cannabis* plant 122 is selected having a cannabinoid profile where the amount of THCa and CBDa is present in a desired ratio. In the example of FIG. 14, the ratio is 3 CBDa to 2THCa. In other examples, the ratio of CBDa to THCa is taken from the group consisting of: 40:1, 35:1, 30:1, 25:1, 20:1, 5:1, 5:2, 5:3, 5:4, 10:1, 4:1, 4:3, 3:1, 3:2, 2:1, 1:1, 1:2, 1:3, 2:3, 3:4, 1:4, 1:10, 4:5, 3:5, 2:5, 1:5, 1:20, 1:25, 1:30, 1:35, 1:40, 0:1, and 1:0. Other ratios of CBDa to THCa are selectable depending on the therapeutic benefits that are desired. In another embodiment, the *cannabis* plant 122 is selected to have one of the cannabinoid profiles shown in table 54 of FIG. 11. In another embodiment, the *cannabis* plant 122 is selected to have one of the cannabinoid profiles shown in table 55 of FIG. 12.

In other embodiments, the cannabinoid profile includes cannabinoids in addition to CBDa and THCa. For example, other cannabinoids include cannabigerolic acid (CBGa), cannabigerovarin acid (CBGVa), tetrahydrocannabinolic acid (THCa), tetrahydrocannabivarin carboxylic acid (THCVa), cannabidiolic acid (CBDa), cannabidivarin acid (CBDVa), cannabichrome carboxylic acid (CBCa), cannabichrome varinic acid (CBCVa), tetrahydrocannabinol (THC), tetrahydrocannabivarin (THCV), tetrahydrocannabivarin acid (THVa), cannabidiol (CBD), cannabidivarin (CBDV), cannabichromene (CBC), cannabichromevarin (CBCV), cannabigerol (CBG), cannabigerovarin (CBGV), cannabinerolic acid (CBNa), cannabigerovarinic acid (CBNVa), cannabinol (CBN), cannabicyclol (CBL), and cannabicyclol acid (CBLa). The cannabinoid profile involves at least one of the above cannabinoids. In other examples, the cannabinoid profile of the selected cannabis plant has at least two of the above cannabinoids present in a desired ratio.

Figure 16:
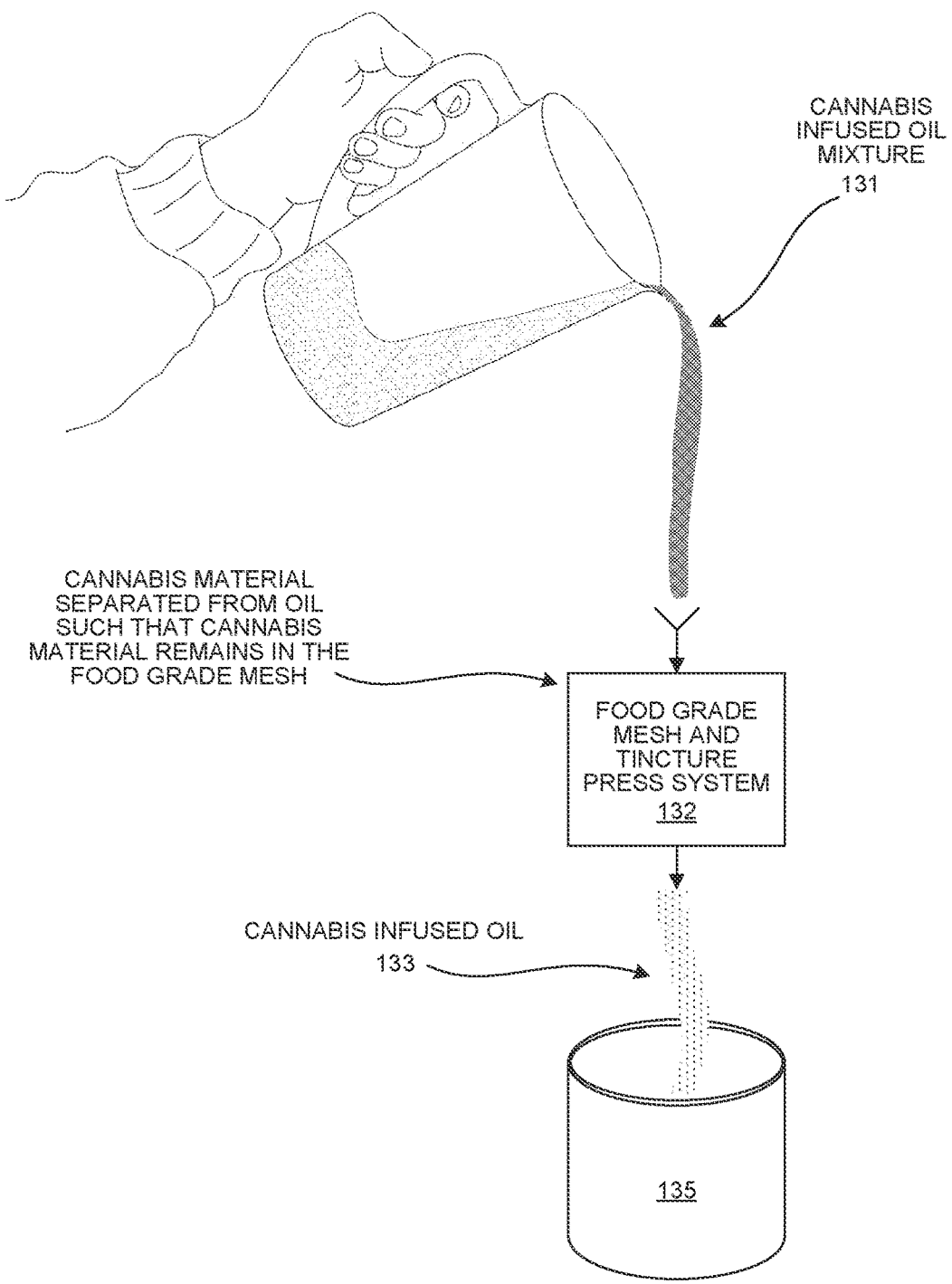

In a second step (step 102), the cannabis material is blended with oil. The mixture is blended without causing the cannabis material to undergo a decarboxylation process thereby obtaining a cannabis infused oil mixture. In the example of FIG. 16, the raw and dried cannabis material 128 is blended with 32 ounces of oil 129 in a high-speed blending appliance 130 for between one and five minutes. Oil 129 is selected from the group consisting of: olive oil, vegetable oil, coconut oil, organic oil, or any other food grade oil. During the blending process, the temperature of the cannabis material is maintained below 125° F. thereby preventing the cannabinoids from decarboxylating.

In addition to blending with oil, lecithin is optionally added during the blending process. The lecithin promotes the bio-availability of cannabinoids in the final oil infusion that is formed using novel method 100. One teaspoon to one tablespoon of soy-based or sunflower-based lecithin is optionally added during the blending process. In another embodiment, the cannabis material is ground after the drying process but before blending with oil. The ground cannabis material is then blended with oil.

In a third step (step 103), the cannabis material is filtered from the cannabis infused oil mixture thereby obtaining a cannabis infused oil. For example, in FIG. 17, the cannabis infused oil mixture 131 is filtered using a food grade mesh and tincture system 132 to separate cannabis material to obtain a cannabis infused oil 133. The extracted cannabis infused oil 133 is stored in container 135 before being packaged into tincture bottles or other types of packaging containers for storage and distribution.

Figure 10:
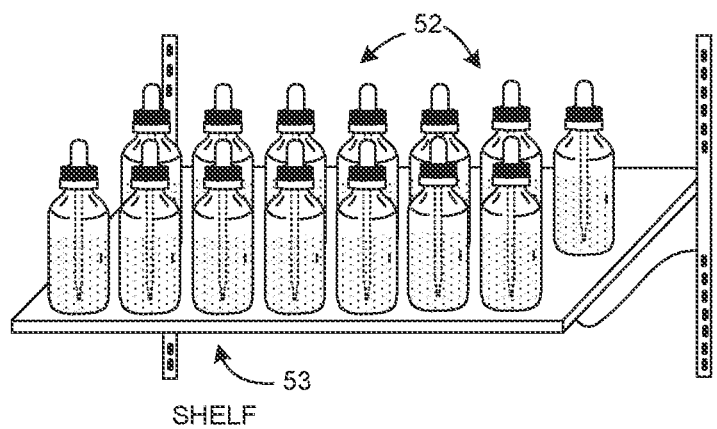
FIG. 10 is a perspective diagram showing how packaged *cannabis* infused oil is stored for distribution.

In a fourth step (step 104), the cannabis infused oil is packaged thereby obtaining a packaged cannabis infused oil without decarboxylated cannabinoids. For example, in FIG. 18, the cannabis infused oil 133 is packaged in a container 134. The cannabis infused oil 133 has between 100 milligrams and 2,000 milligrams of cannabinoids per fluid ounce of cannabis infused oil 133. The resulting packaged cannabis infused oil is stored in accordance with method 50 of FIG. 9 and as shown in FIG. 10.

FIG. 18 is a flowchart of a method 200 in accordance with another embodiment. The method 200 provides a technique to obtain an amount of cannabis material having a desired cannabinoid profile without having to undergo a costly process of developing a strain of cannabis plant with the desired cannabinoid profile. In addition, the cost of testing strains and cannabis products is costly. The method 200 avoids the costs associated with developing new strains and costs of laboratory studies to ascertain cannabinoid profiles. The method 200 provides a novel technique of selecting two amounts of cannabis profiles having different cannabinoid profiles and combining them to obtain an amount of cannabis material having the desired cannabinoid profile.

In a first step (step 201), a first amount of cannabis material having a first cannabinoid profile is combined with a second amount of cannabis material having a second cannabinoid profile. A third amount of cannabis material having a desired cannabinoid profile is obtained. In the example of FIG. 19, a first cannabis oil 202 having a first cannabinoid profile is combined with a second cannabis oil 203 having a second cannabinoid profile. A third amount of cannabis oil 204 is obtained that has the desired cannabinoid profile. The amount of the first cannabis oil 202 and the amount of the second cannabis oil 203 to be combined together are determined based on the first cannabinoid profile, the second cannabinoid profile, and the cannabinoid profile that is desired. The cannabis material having the desired cannabinoid profile is packaged into a packaged cannabis material 205. The packaged cannabis material 205 having the desired cannabinoid profile is formed without having to have developed a cannabis strain having the desired cannabinoid profile.

Although certain specific embodiments are described above for instructional purposes, the teachings of this patent document have general applicability and are not limited to the specific embodiments described above. In another embodiment, high concentrate cannabis paste is used as the cannabis base instead of raw cannabis plant material. The high concentrate cannabis paste can be raw cannabis paste extract that is created from ethanol distillation or $CO_2$ high pressure extraction as long as it was created at low temperatures that preserve the raw cannabinoids without undesirably decarboxylating the cannabinoids.

In another embodiment, the cannabis infused oil is formed such that there are at least two cannabinoids in the oil. The two cannabinoids are present in the oil in accordance with a cannabinoid profile such that an amount of the first of the cannabinoids present in the cannabis infused oil is less than a first percentage of the total amount of cannabinoids in the oil and an amount of the second of the cannabinoids present in the cannabis infused oil is less than a second percentage of the total amount of cannabinoids in the oil. A sum of the first percentage and the second percentage is less than or equal to one-hundred. The first percentage and the second percentage are determined before the cannabis infused oil is manufactured. In yet another embodiment, the cannabis infused oil is formed such that there are at least two cannabinoids in the oil. The two cannabinoids are present in the oil in accordance with a cannabinoid profile such that an amount of the first of the cannabinoids present in the cannabis infused oil is greater than a first percentage of the total amount of cannabinoids in the oil and an amount of the second of the cannabinoids present in the cannabis infused oil is greater than a second percentage of the total amount of cannabinoids in the oil. The first percentage and the second percentage are determined before the cannabis infused oil is manufactured.

Figure 7:
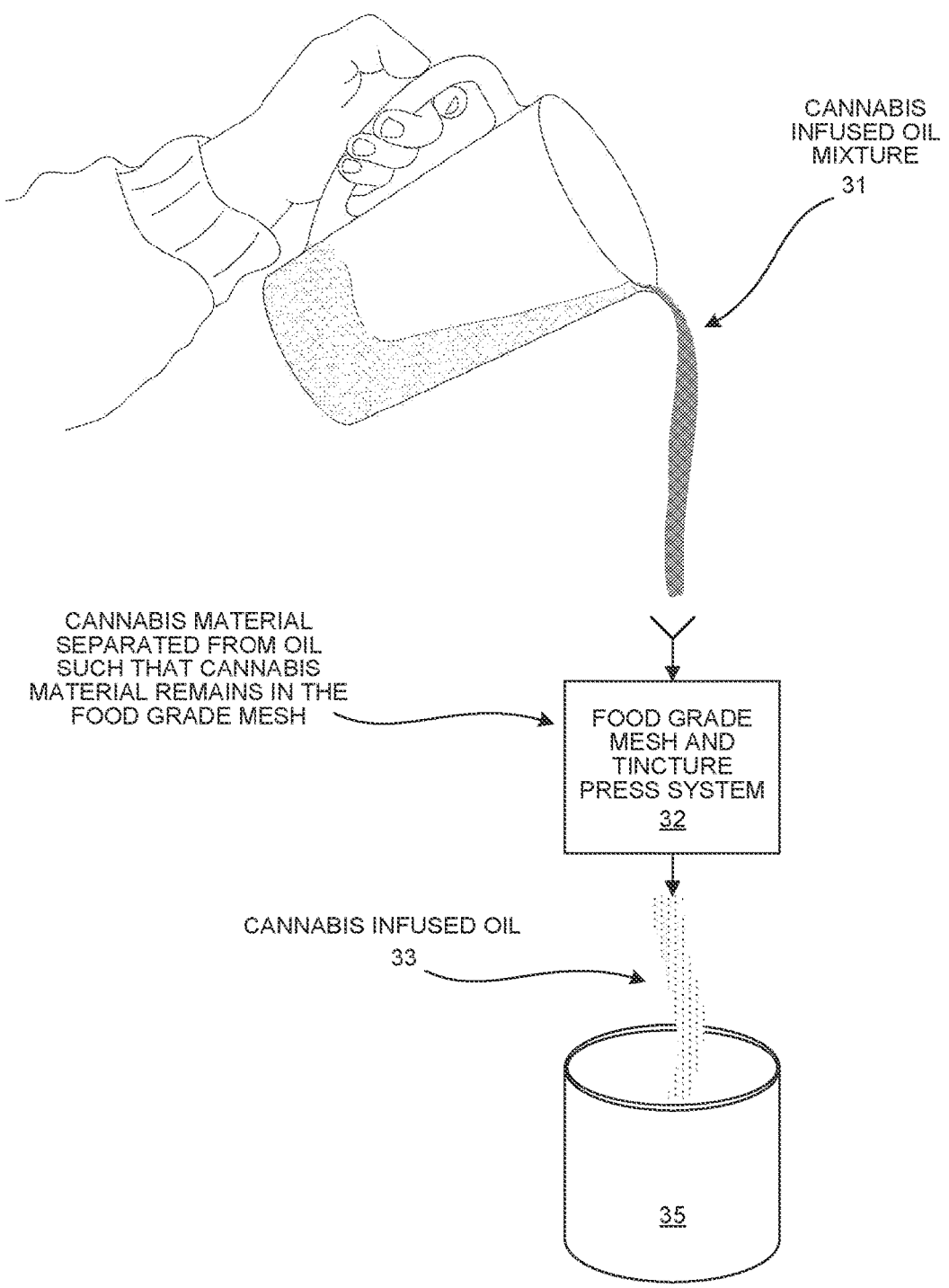
FIG. 7 is a perspective diagram showing how *cannabis* material is separated from the oil to obtain a *cannabis* infused oil as in a fifth step of method 10.

The filter process in which the cannabis infused oil 133 is extracted from the cannabis infused oil mixture 131 is performed manually in FIGS. 7 and 16. It is understood that such process can be automated and scaled to satisfy commercial demands and avoid the need for manual supplying into the food grade mesh and tincture system 132. It is also understood that other filtration techniques may be employed that do not involve the food grade mesh and tincture system 132. In addition, a preservative is optionally added to the cannabis infused oil prior to packaging. The preservative may be added before blending, during blending, or after blending. The preservative is selected from the group consisting of citric acid, rosemary oil, organic oil, or another food grade preservative. Accordingly, various modifications, adaptations, and combinations of various features of the described embodiments can be practiced without departing from the scope of the invention as set forth in the claims.

What is claimed is:

1. A method comprising:
obtaining cannabis paste having a cannabinoid profile, wherein the cannabinoid profile comprises an amount of cannabinoids; and
blending the cannabis paste with oil thereby obtaining a cannabis infused oil.

2. The method of claim 1, further comprising:
packaging the cannabis infused oil thereby obtaining a packaged cannabis infused oil.

3. The method of claim 1, wherein a temperature of the cannabis paste remains below 125° F.

4. The method of claim 1, wherein the cannabis infused oil has between 100 milligrams and 10,000 milligrams of cannabinoids per fluid ounce of cannabis infused oil.

5. The method of claim 1, wherein the blending extends for a period of between one and thirty minutes.

6. The method of claim 1, wherein the amount of cannabinoids includes an amount of cannabidiolic acid (CBDa), wherein the amount of CBDa in the cannabis infused oil is at least a pre-determined percentage of the total cannabinoids in the cannabis infused oil, and wherein the pre-determined percentage is taken from the group consisting of: 5%, 10%, 20%, 25%, 30%, 33.33%, 40%, 50%, 60%, 66.66%, 70%, 75%, 80%, 90%, 95%, and 99%.

7. The method of claim 1, wherein the amount of cannabinoids includes at least one cannabinoid taken from the group consisting of: cannabigerolic acid (CBGa), cannabigerovarin acid (CBGVa), tetrahydrocannabinolic acid (THCa), tetrahydrocannabivarin carboxylic acid (THCVa), cannabidiolic acid (CBDa), cannabidivarin acid (CBDVa), cannabichrome carboxylic acid (CBCa), cannabichrome varinic acid (CBCVa), tetrahydrocannabivarin acid (THVa), cannabinerolic acid (CBNa), cannabigerovarinic acid (CBNVa), and cannabicyclol acid (CBLa).

8. The method of claim 1, wherein the cannabinoid profile includes cannabidiolic acid (CBDa) and tetrahydrocannabinolic acid (THCa) having a ratio of CBDa to THCa that is taken from the group consisting of: 40:1, 35:1, 30:1, 25:1, 20:1, 5:1, 5:2, 5:3, 5:4, 10:1, 4:1, 4:3, 3:1, 3:2, 2:1, 1:1, 1:2, 1:3, 2:3, 3:4, 1:4, 1:10, 4:5, 3:5, 2:5, 1:5, 1:20, 1:25, 1:30, 1:35, 1:40, 0:1, and 1:0.

9. The method of claim 1, wherein the blending involves adding lecithin in addition to oil, wherein the lecithin is taken from the group consisting of sunflower lecithin and soy lecithin.

10. The method of claim 1, wherein the oil is taken from the group consisting of: olive oil, vegetable oil, coconut oil, organic oil, and another type of food grade oil.

11. A packaged cannabis infused oil comprising:
a container; and
a cannabis infused oil disposed within the container, wherein the cannabis infused oil includes an amount of cannabinoids, wherein the amount of cannabinoids are present in the cannabis infused oil in accordance with a cannabinoid profile determined before the cannabis infused oil is formed, and wherein the cannabis infused oil is formed by blending cannabis paste with oil to obtain a cannabis infused oil mixture.

12. The packaged cannabis infused oil of claim 11, wherein the cannabis infused oil has between 100 milligrams and 10,000 milligrams of cannabinoids per fluid ounce of cannabis infused oil.

13. The packaged cannabis infused oil of claim 11, wherein at no point during manufacture of the cannabis infused oil does a temperature of cannabis material rise above 125° F.

14. The packaged cannabis infused oil of claim 11, wherein the amount of cannabinoids includes at least one cannabinoid taken from the group consisting of: cannabigerolic acid (CBGa), cannabigerovarin acid (CBGVa), tetrahydrocannabinolic acid (THCa), tetrahydrocannabivarin carboxylic acid (THCVa), cannadidiolic acid (CBDa), cannabidivarin acid (CBDVa), cannabichrome carboxylic acid (CBCa), cannabichrome varinic acid (CBCVa), tetrahydrocannabivarin acid (THVa), cannabinerolic acid (CBNa), cannabigerovarinic acid (CBNVa), and cannabicyclol acid (CBLa).

15. The packaged cannabis infused oil of claim 11, wherein the cannabinoid profile includes cannabidiolic acid (CBDa) and tetrahydrocannabinolic acid (THCa) having a ratio of CBDa to THCa that is taken from the group consisting of: 40:1, 35:1, 30:1, 25:1, 20:1, 5:1, 5:2, 5:3, 5:4, 10:1, 4:1, 4:3, 3:1, 3:2, 2:1, 1:1, 1:2, 1:3, 2:3, 3:4, 1:4, 1:10, 4:5, 3:5, 2:5, 1:5, 1:20, 1:25, 1:30, 1:35, 1:40, 0:1, and 1:0.

16. The packaged cannabis infused oil of claim 11, wherein the cannabis infused oil further comprises a lecithin that is taken from the group consisting of: sunflower lecithin and soy lecithin.

17. The packaged cannabis infused oil of claim 11, wherein the oil is taken from the group consisting of: olive oil, vegetable oil, coconut oil, organic oil, and food grade oil.

18. The packaged cannabis infused oil of claim 11, wherein the amount of cannabinoids includes an amount of cannabidiolic acid (CBDa), wherein the amount of CBDa in the cannabis infused oil is at least a pre-determined percentage of the total cannabinoids in the cannabis infused oil, and wherein the pre-determined percentage is taken from the group consisting of: 5%, 10%, 20%, 25%, 30%, 33.33%, 40%, 50%, 60%, 66.66%, 70%, 75%, 80%, 90%, 95%, and 99%.

19. A method comprising:
obtaining cannabis paste having a cannabinoid profile, wherein the cannabinoid profile comprises an amount of cannabinoids;
combining the cannabis paste having the cannabinoid profile with an alcohol thereby obtaining an alcohol and cannabis paste mixture; and
blending the alcohol and cannabis paste mixture with oil thereby obtaining a cannabis infused oil.

20. The method of claim 19, wherein a temperature of the alcohol and cannabis paste mixture remains below 125° F.

* * * * *